United States Patent [19]
Schmitz

[11] Patent Number: 5,283,711
[45] Date of Patent: Feb. 1, 1994

[54] CAPACITIVE HUMIDITY SENSOR

[75] Inventor: Pieter P. J. Schmitz, Alphen aan den Rijn, Netherlands

[73] Assignee: Flucon B.V., Alphen aan den Rijn, Netherlands

[21] Appl. No.: 720,430
[22] PCT Filed: Dec. 28, 1989
[86] PCT No.: PCT/NL89/00100
 § 371 Date: Aug. 22, 1991
 § 102(e) Date: Aug. 22, 1991
[87] PCT Pub. No.: WO90/07708
 PCT Pub. Date: Jul. 12, 1990

[30] Foreign Application Priority Data

Dec. 30, 1988 [NL] Netherlands .................. 8803223

[51] Int. Cl.$^5$ .................. H01G 5/20; H01G 5/28
[52] U.S. Cl. .................. 361/286; 324/689; 73/335.04
[58] Field of Search .................. 361/286; 324/689; 73/335.04; 29/25.42; 338/35

[56] References Cited
U.S. PATENT DOCUMENTS
4,438,480 3/1984 Chambaz et al. .................. 361/286
4,564,882 1/1986 Baxter et al. .................. 361/286

FOREIGN PATENT DOCUMENTS
0094266 11/1983 European Pat. Off. .
3203990 8/1983 Fed. Rep. of Germany .
2327536 5/1977 France .
2554593 5/1985 France .
1223117 4/1986 U.S.S.R. .
2159956 12/1985 United Kingdom .

Primary Examiner—Bruce A. Reynolds
Assistant Examiner—Michael D. Switzer
Attorney, Agent, or Firm—Bachman & LaPointe

[57] ABSTRACT

Capacitive humidity sensor comprising a substrate, a moisture-impermeable conducting bottom layer as first capacitor plate, a dielectric layer, and a moisture-permeable conducting top layer as second capacitor plate, and connecting wires associated with the first and second capacitor plates, whereby the change in the dielectric constant, and therefore in the capacitance value, due to absorption of water molecules is measured. The substrate is a flexible copper laminate in which at least the conducting bottom layer is etched, and the conducting top layer comprises a solid printed layer having a conducting grid pattern, which is printed with conducting ink.

6 Claims, 1 Drawing Sheet

CAPACITIVE HUMIDITY SENSOR

BACKGROUND OF THE INVENTION

The invention relates to a capacitive humidity sensor comprising a substrate being a flexible copper laminate, a moisture-impermeable conducting bottom layer etched in said copper laminate as first capacitor plate, a dielectric layer of which the dielectric constant is a function of moisture absorption, and a moisture-permeable conducting top layer as second capacitor plate, said bottom layer and a contact layer making contact with the moisture-permeable top layer and being deposited adjacent each other and isolated from each other on the substrate, the top layer extending both over the dielectric layer and over the contact layer. Such a humidity sensor is disclosed in European patent application 0094266.

In such a sensor, which in fact consists of an electrical capacitor, the humidity is determined by measuring the change in dielectric constant of the dielectric medium, and therefore the change in capacitance value, due to the absorption of water molecules by the dielectric material. If, for example, the material of a dry dielectric layer has a dielectric constant of 3.5 and water approximately has one of 80, it will be clear that the change in capacitance value due to moisture absorption may be appreciable. In order that moisture or water can be absorbed by the dielectric layer, the top layer has to be moisture-permeable.

This known sensor has a substrate on which a copper layer as first capacitor plate is deposited. A moisture-impermeable insulating layer is provided on top of the first capacitor plate. Said insulating layer serves as a barrier layer and prevents resistance loss across the dielectric medium at high relative humidity, or even short circuiting between the plates regardless of the structure of the dielectric medium. The dielectric layer mentioned is sufficiently porous to absorb moisture.

Now in practice it appears that the use of such a sensor is strictly dependent on well-defined precalibration techniques under dry and moist atmospheric conditions before using it for the consumer market and for industrial application.

The object of the invention is to eliminate the above mentioned problem and to provide a cheap sensor which is most robust and which can be easily calibrated after manufacture.

SUMMARY OF THE INVENTION

According to the invention this is achieved in a capacitive humidity sensor of the type mentioned above in that the top layer comprises a solid printed grid pattern of conducting ink, and a row of small conducting ink areas at at least one side of the grid pattern.

In an advantageous embodiment of the above sensor at least between the bottom layer and the dielectric layer a moisture-impermeable insulating layer or barrier layer is provided, whereby in one case the row of small ink areas is provided above the insulating layer and in another case two rows of small ink areas on either side are provided of which one is above the insulating layer and the other is above the dielectric layer.

In this embodiment according to the invention, an exceptionally cheap sensor for the consumer market is obtained which is also suitable for industrial applications. This sensor according to the invention can be calibrated simply, both under dry and moist atmospheric conditions. For calibration in the case of a dry reference environment, several of the small areas of the row above the barrier layer are connected to the main grid by means of small pads of conducting ink in order to obtain the required fixed (dry) capacitance value. For further calibration in the case of a humid reference environment, small areas of the row above the dielectric or active layer are connected to the main grid in order to adjust the required delta capacitance value. For this calibration, it is assumed that it is easier to add than to subtract a capacitance value. Such a subtraction may, however, also be achieved by laser trimming. After trimming, the conducting ink tracks can be hardened. The advantages of this "printing" method are that the exact printing geometry can be defined and there is no dependence on fortuitous phenomena. Trimming can be carried out both for the fixed and the delta values. If process faults are made during printing, these can be "erased", the more expensive part of the substrate clad with the barrier layer being left intact.

From French patent application 2327536 a capacitive humidity sensor is known consisting of a simple structure of a copper plate as first capacitor plate, dielectric paper as dielectric medium and an upper capacitor plate which consists of a copper wire grid. Said wire grid is fastened with the aid of plastic screws to the first capacitor plate. This humidity sensor is intended to detect the presence of oil in gas.

From German patent application 3203990 a method is known for adjusting the capacity of a capacitive humidity sensor. This adjustment is performed by using a laser beam to remove or trim the conducting upper capacitor plate consisting of a gold film. This is performed at high temperature in order to cause the remaining moisture, still present in the dielectric medium, to be negligibly small.

BRIEF DESCRIPTION OF THE DRAWINGS

The invention will be explained in more detail on the basis of an exemplary embodiment with reference to the drawing, in which.

DESCRIPTION OF THE PREFERRED EMBODIMENTS

As stated above, the object of the invention is to provide a cheap sensor for consumer applications.

According to the invention, the glass substrate material, which is per se an excellent material, is now replaced in practice by copper laminate which is frequently used, for example, in printed circuit boards (PCBs). In a further embodiment, said copper laminate may be constructed with polysiloxane-glass textile or fabric. The moisture-impermeable bottom layer can be etched on the copper surface of such a laminate as first capacitor plate, if necessary with a second thinner contact plate next to it which acts as contact plate for the moisture-permeable top layer. Connecting wires can be attached to said bottom layer and contact layer in a later phase of the manufacture.

The use of such a thin flexible PCB laminate has the advantage that use can be made of PCB manufacturing techniques, the finished result also yielding a more robust sensor than the one manufactured from thin-film glass substrates. It is then possible to start with larger substrates, for example, resulting in a quantity of 50×50=2500 sensors. Under certain conditions, in which an insulating polymer is deposited as insulating layer on the moisture-impermeable bottom layer, it is possible in practice to process two substrates simultaneously back to back, as a result of which a quantity of 5000 sensors can be produced in one processing phase.

Figure 1:
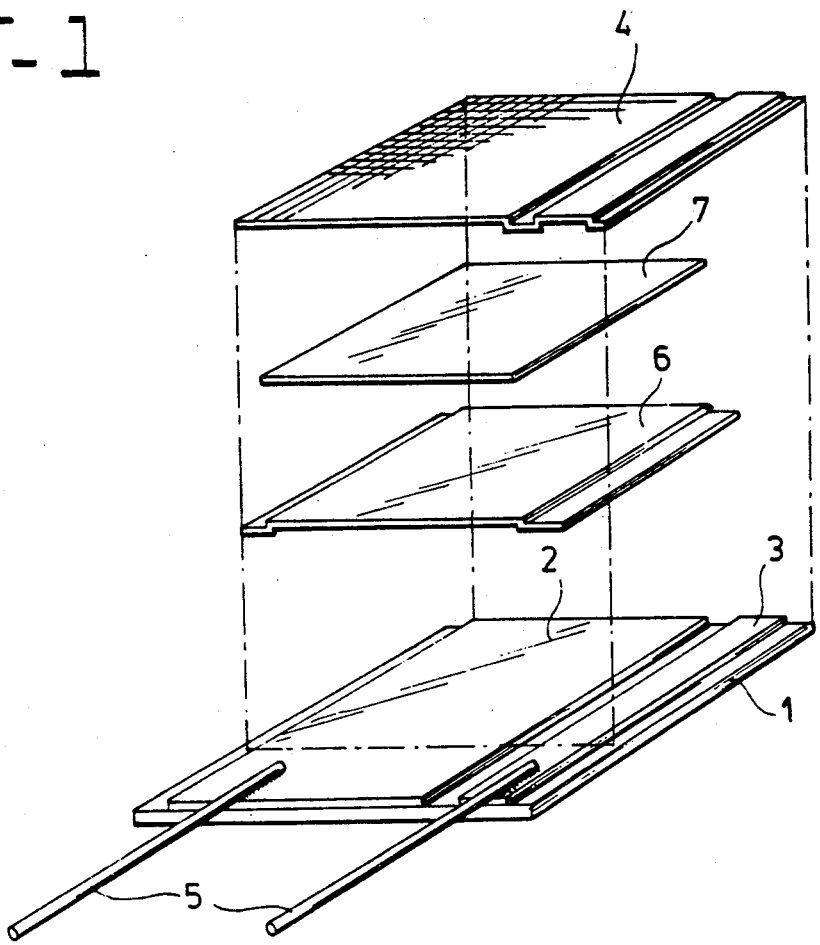
FIG. 1 shows a perspective view of the layered structure of the exemplary embodiment of a sensor according to the invention.

FIG. 1 shows diagrammatically the structure of a sensor according to the invention.

1 indicates the substrate consisting of a thin PCB copper laminate in which two copper layers 2 and 3 are etched. The layer 2 indicated at the left-hand side is the moisture-impermeable layer which acts as first capacitor plate and the layer 3 is the contact plate which makes contact with the moisture-permeable top layer 4, which acts as second capacitor plate, in a later phase of the manufacture. When the substrate is cut up in a final phase and the individual sensors are separated, the connecting wires 5 are attached to the layers 2 and 3.

6 indicates a polymer coating which functions as insulating layer and which, although extremely thin, protects the surface of the active copper capacitor plate 2 against attack and contamination. Since the layer 6 is itself moisture-impermeable, any short circuiting between the capacitor plates mentioned is consequently prevented, regardless of the structure of the dielectric material, and direct current, which would otherwise produce polarization drift as a consequence of electrolysis, is prevented from flowing. The layer will prevent breakdown occurring as a consequence of the occurrence of so-called "pinholing" in the active dielectric 7. The polymer 6 does not extend over the thinner copper contact layer 3. In the latter case, an inert, non-reactive pinhole-free barrier polymer is preferably used.

The dielectric layer 7 is composed of an active polymer which can be spun, can be deposited by means of screen printing or in another manner, so that an extremely thin layer is produced which nevertheless contains a sufficient quantity of pores required for the operation of the humidity sensor. In this manner, a dielectric "sponge" is obtained which ensures a rapid change in the capacitance value under the influence of moisture. A large "inhalation" and "exhalation" surface is consequently achieved. The figure indicates that the layer 7 does not extend far enough to lie on top of the contact layer 3. But other methods of manufacture are conceivable.

4 indicates the moisture-permeable top layer as second capacitor plate which extends over the whole. The part of said top layer extending over the dielectric layer 7 has the form of a grid printed on the dielectric layer with conducting ink.

Figure 2:
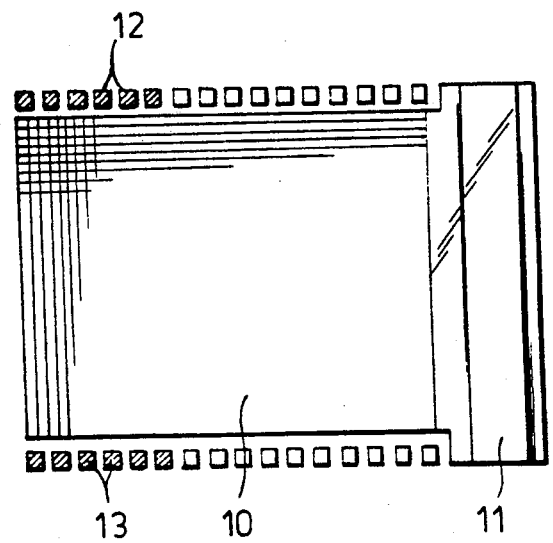
FIG. 2 shows a plan view of the top layer, which acts as second capacitor plate, of the exemplary embodiment of FIG. 1.

The plan view shown in FIG. 2 shows the top plate 4 mostly as a rectangular grid pattern, although other patterns are also possible. The grid openings ensure moisture transmission. The geometry of the grid 10 is important. A maximum (conducting) ink surface area will produce a maximum capacitance value, but then the time necessary for absorption and desorption will be large, unless the moisture-transmitting surface area is sufficiently large. A good result is produced with a relatively large sensor surface area, such as, for example, 10 mm$^2$, in which case the response time is adversely affected to a certain extent.

11 indicates the part of the top plate which is in solid printed form, i.e. does not have any openings, and which is intended to make contact with the contact layer 3 on the substrate 1.

12 indicates a row of small conducting printed areas in an insulated arrangement. In constructing the capacitor, it is intended that said row of small areas 12 is situated only above the barrier polymer and not above the active polymer. The capacitances thereby formed have a minimum or zero value.

In manufacture, the design is such that the sensor lies somewhat below its normal tolerance of capacitance values, both under dry and moist conditions (delta=0% to 100% relative humidity range). For automatic calibration, several of the small areas 12 are connected in the case of a dry reference environment to the main grid by means of small pads of conducting ink in order to obtain the required fixed (dry) capacitance value.

13 indicates another row of small conducting printed areas in an insulated arrangement. In the construction of the capacitor, however, these are situated above the active polymer. These small areas can also be connected to the main grid in order to adjust the required delta capacitance value in a humid or moist reference environment.

In the above, it has been assumed that it is easier to add than to subtract a capacitance value. Such a subtraction may, however, also be achieved by laser trimming.

After trimming, the conducting ink tracks can be hardened. The advantages of this "printing" method are that the exact printing geometry can be defined and there is no dependence on fortuitous phenomena. Trimming can be carried out both for the fixed and the delta values. If process faults are made during printing, these can be "erased", the more expensive part of the substrate clad with the barrier polymer being left intact.

The small trimming areas are shown as small squares. It will be clear that they can also be provided in a smaller number and, for example, in a binary surface area progression.

During manufacture, sensors can be manufactured in accordance with the required application having an improved response speed by making one dimension greater, as a result of which a longer sensor is obtained. Since the contact surface occupies an appreciable part of the total surface, a more slender design will make it possible for the contact surface area to decrease in favor of a larger active surface area.

Since the barrier polymer is expensive, the copper laminate is preferably clad only on one side. This can best be achieved by processing the substrate plates two at a time, back to back. To do this, it is necessary to mask the contact layer or even to grind off the barrier layer obtained. Since the laminates can be obtained processed on both sides, it is possible to provide both contact layers on the other side, unclad by the barrier layer and consequently readily solderable and to connect them by means of through-hole plating or by means of specially designed "knife-edge" contact terminals.

All the inactive surfaces which are not covered by the barrier polymer can be covered with solder resist in the normal manner of protecting PCB laminates.

The cheap humidity sensor specified above, which can be manufactured in a reproducible manner, may be used for many types of applications, such as for air treatment systems, in the motor vehicle industry for window demisting systems, brake (shoe) systems and for internal combustion engines in which the combustion process is strongly dependent on the relative humidity.

I claim:

1. Capacitive humidity sensor comprising a substrate being a flexible copper laminate, a moisture-impermeable conducting bottom layer etched in said copper laminate as first capacitor plate, a dielectric layer of which the dielectric constant is a function of moisture absorption, and a moisture-permeable conducting top layer as second capacitor plate, said bottom layer and a contact layer making contact with the moisture-permeable top layer being deposited adjacent each other and isolated from each other on the substrate, the top layer extending both over the dielectric layer and over the contact layer, wherein the top layer comprises a solid printed grid pattern of conducting ink, and a row of small conducting ink areas at at least one side of the grid pattern.

2. Capacitive humidity sensor according to claim 1, wherein at least between the bottom layer and the dielectric layer a moisture-impermeable insulating layer is provided, and the row of small ink areas of the top layer is situated above the insulating layer and not above the dielectric layer, so that for precalibration of the capacitance value of the sensor in a dry atmosphere small ink areas can be connected to the grid pattern.

3. Capacitive humidity sensor according to claim 1, wherein at least between the bottom layer and the dielectric layer a moisture-impermeable insulating layer is provided, and the row of small ink areas of the top layer is situated above the dielectric layer and not above the insulating layer, so that for precalibration of the capacitance value of the sensor in a moist atmosphere small ink areas can be connected to the grid pattern.

4. Capacitive humidity sensor comprising a substrate, a moisture-impermeable conducting bottom layer as first capacitor plate, a dielectric layer, and a moisture-permeable conducting top layer as second capacitor plate, and connecting wires associated with the first and second capacitor plates, the change in the dielectric constant, and therefore in the capacitance value, due to absorption of water molecules being measured, the substrate being a flexible copper laminate in which at least the conducting bottom layer mentioned is etched, the conducting top layer comprising a solid printed layer having a conducting grid pattern with sides thereof, the bottom layer and a contact layer making contact with the moisture-permeable top layer being deposited parallel to each other on the substrate, a moisture-impermeable insulating layer being present at least between the bottom layer and the dielectric layer, wherein the top layer has a row of small ink areas at at least one of the sides of the grid pattern.

5. Capacitive humidity sensor according to claim 4, wherein the row of small ink areas in the sensor is situated such that the dielectric layer is not situated under the row of small ink areas but the insulating layer is, so that, during precalibration of the capacitance value in a dry atmosphere, small ink areas can be connected, if necessary, to the grid pattern.

6. Capacitive humidity sensor according to claim 4, wherein the row of small ink areas in the sensor is situated such that the dielectric layer is situated under the row of small ink areas and the insulating layer is not, so that, during precalibration of the capacitance value in a moist atmosphere, small ink areas can be connected, if necessary, to the grid pattern.

* * * * *